(12) United States Patent
Catinat et al.

(10) Patent No.: US 7,323,578 B2
(45) Date of Patent: Jan. 29, 2008

(54) PROCESS FOR MANUFACTURING AN OXIRANE

(75) Inventors: Jean-Pierre Catinat, Waudrez (BE); Michel Strebelle, Brussels (BE)

(73) Assignee: Solvay (Societe Anonyme), Brussels (BE)

( * ) Notice: Subject to any disclaimer, the term of this patent is extended or adjusted under 35 U.S.C. 154(b) by 751 days.

(21) Appl. No.: 10/476,879

(22) PCT Filed: May 10, 2002

(86) PCT No.: PCT/EP02/07251

§ 371 (c)(1),
(2), (4) Date: Nov. 13, 2003

(87) PCT Pub. No.: WO02/092586

PCT Pub. Date: Nov. 21, 2002

(65) Prior Publication Data

US 2006/0122409 A1 Jun. 8, 2006

(30) Foreign Application Priority Data

May 14, 2001 (FR) .................................. 01 06349

(51) Int. Cl.
*C07D 301/12* (2006.01)
(52) U.S. Cl. ...................... 549/529; 549/531
(58) Field of Classification Search ................ 549/529, 549/531
See application file for complete search history.

(56) References Cited

U.S. PATENT DOCUMENTS

| 5,780,655 | A | 7/1998 | Shum |
| 6,429,322 | B1 | 8/2002 | Catinat et al. |
| 6,590,112 | B1 | 7/2003 | Catinat et al. |
| 2005/0054864 | A1 | 3/2005 | Strebelle et al. |

FOREIGN PATENT DOCUMENTS

| DE | 197 23 950 | 12/1998 |
| DE | 199 62 720 | 6/2001 |
| EP | 0 230 949 | 8/1987 |
| EP | 0 712 852 | 5/1996 |
| EP | 0 757 043 | 2/1997 |
| WO | 99 48882 | 9/1999 |
| WO | 99 48883 | 9/1999 |

*Primary Examiner*—Amelia A. Owens
(74) *Attorney, Agent, or Firm*—Oblon, Spivak, McClelland, Maier & Neustadt, P.C.

(57) ABSTRACT

Process for manufacturing an oxirane by reaction between an olefin and a peroxide compound in a reactor containing a liquid phase, in the presence of water, one or more organic solvents, a catalyst and one or more compounds for increasing the selectivity of the catalyst toward epoxidation reactions, in which: if the process is performed in batchwise mode, the liquid phase present in the reactor when the reaction starts, if the process is performed continuously, all of the liquid phases that are fed continuously into the reactor has/have a total organic solvent content of at least 0.1 g/kg and of not more than 675 g/kg.

18 Claims, 1 Drawing Sheet

PROCESS FOR MANUFACTURING AN OXIRANE

Figure 1:
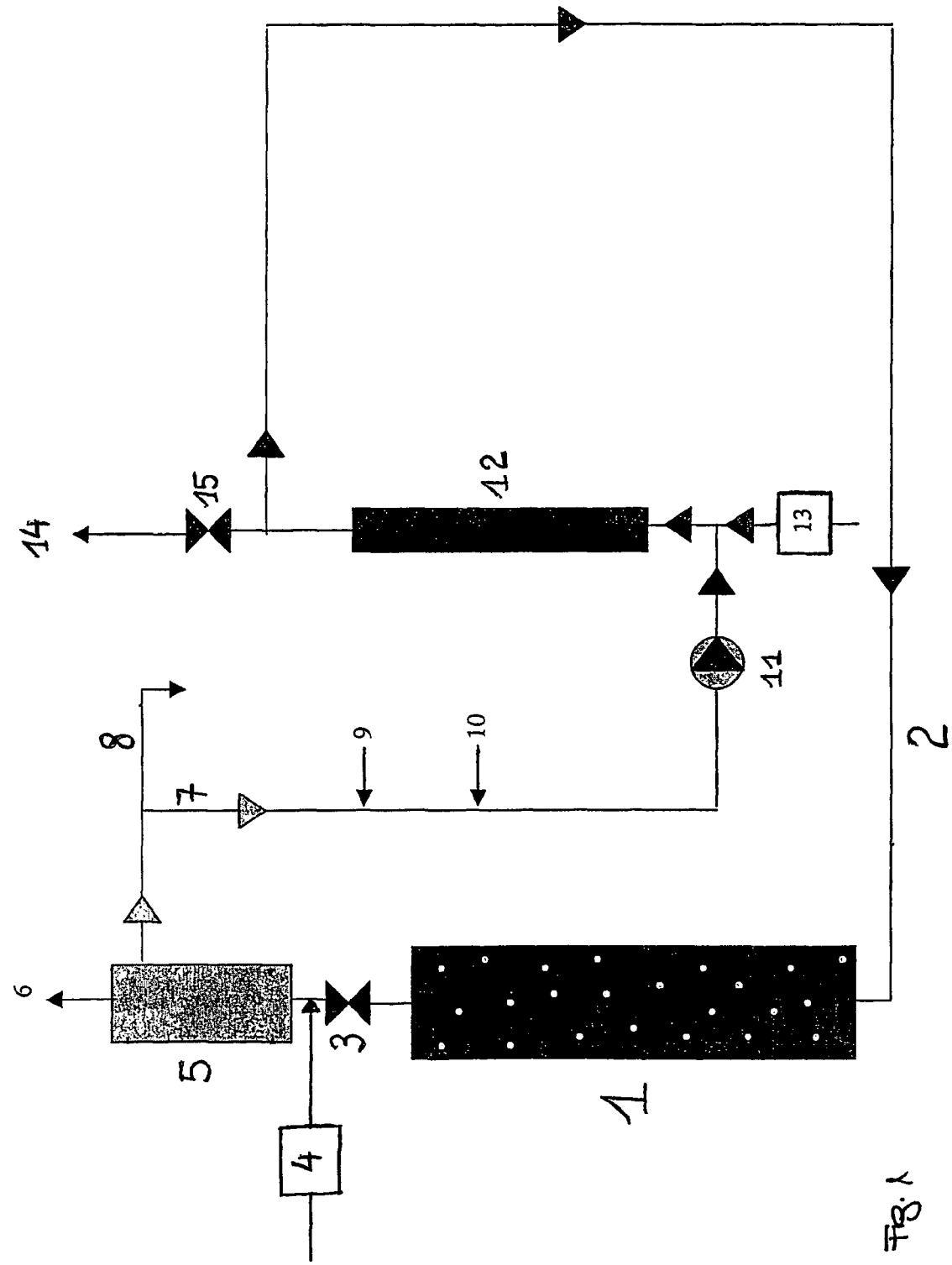

The invention relates to a process for manufacturing an oxirane by reaction between an olefin and a peroxide compound in the presence of a zeolite-based catalyst. The invention relates more particularly to a process for manufacturing 1,2-epoxypropane (or propylene oxide) by reaction between propylene and hydrogen peroxide, and to a process for manufacturing 1,2-epoxy-3-chloropropane (or epichlorohydrin) by reaction between allyl chloride and hydrogen peroxide.

It is known practice to manufacture propylene oxide by epoxidation of propylene using hydrogen peroxide in the presence of a catalyst of TS-1 type, as described, for example, in patent application EP 0 230 949. This known process has the drawback of leading, under certain conditions, to low selectivities and to a deactivation of the catalyst.

It is also known practice to add to the reaction medium various additives that interact with the acidic sites of the catalyst and, in so doing, make it possible to increase the selectivity thereof toward epoxidation reactions. Thus, patent applications EP 0 712 852 and EP 0 757 043 describe for this reaction the use of a metal salt, but such additions generally result in a reduction in the activity, and, what is more, the reaction conditions used make it necessary periodically or very frequently to regenerate the catalyst, following its deactivation.

The invention is directed toward overcoming this drawback by providing a process for manufacturing an oxirane that shows both a high selectivity and a high conversion, as well as a minimum deactivation of the catalyst.

The invention consequently relates to a process for manufacturing an oxirane by reaction between an olefin and a peroxide compound in a reactor containing a liquid phase, in the presence of water, one or more organic solvents, a catalyst and one or more compounds for increasing the selectivity of the catalyst toward epoxidation reactions, in which:

if the process is performed in batchwise mode, the liquid phase present in the reactor when the reaction starts if the process is performed continuously, all of the liquid phases that are fed continuously into the reactor has/have a total organic solvent content of at least 0.1 g/kg and of not more than 675 g/kg.

The invention is based on the surprising observation that, in the presence of an organic solvent content that is lower than those generally recommended, both a high selectivity and a high conversion rate (activity) are obtained. Thus, according to the invention, it is important that, in the case of a batchwise process, it is the liquid phase present in the reactor during the start of the reaction that satisfies this condition, whereas, in the case of a continuous process, it is the liquid phase fed continuously into the reactor that satisfies it. It should be noted in this respect that this liquid phase may be fed in one or more flows into the reactor and that, in the latter case, it is the total organic solvent content relative to all of the liquids fed into the reactor that is concerned.

In the text hereinbelow, the expression "reaction medium" is intended to denote the liquid phase present in the reactor and containing the olefin, the peroxide compound, the water, the organic solvent(s), the compound(s) for increasing the selectivity of the catalyst, the oxirane formed and dissolved, and any by-products.

One of the essential characteristics of the invention lies in the addition, to the liquid phase in which the reaction proceeds, of a compound for effectively limiting the side reactions that give rise to the formation of undesired by-products, and thus for increasing the selectivity of the catalyst toward the epoxidation reactions. This compound may be chosen from mineral or organic bases, mixtures of a salt and of its conjugate acid or base (known as "buffer mixtures"), salts, and mixtures thereof Examples of mineral bases are strong bases such as NaOH and KOH, or weak bases such as $NH_4OH$. Examples of organic bases are organic molecules comprising one or more nitrogenous groups, for instance an amine group (for example ethanolamine) or an amide group in which the nitrogen atom optionally bears at least one hydrogen atom (for example urea), and nitriles (for example acetonitrile). An example of a buffer mixture that is very suitable is a mixture of ammonium chloride and ammonia. Examples of salts are basic, acidic or neutral, organic or inorganic metal salts. It may also be an ammonium salt. Generally, the metal is chosen from alkali metals and alkaline-earth metals. The alkali metals most often used are lithium, sodium, potassium and cesium. Sodium is preferred. The alkaline-earth metals that may be used are mainly magnesium, calcium, strontium and barium. The salts that may be used are mainly the halides, oxides, hydroxides, carbonates, sulfates, phosphates and salts of organic acids, such as acetates. The halides are generally fluorides, chlorides, bromides and iodides. A preference is shown for chlorides.

The amount of compound for increasing the selectivity of the catalyst used in the process according to the invention is generally greater than or equal to $10^{-6}$ mol per kg of reaction medium, advantageously greater than or equal to $10^{-5}$ mol/kg of reaction medium and preferably greater than or equal to $10^{-4}$ mol/kg of reaction medium. The amount is usually less than or equal to 2 mol/kg of reaction medium, in particular less than or equal to 1 mol/kg of reaction medium and more especially less than or equal to 0.5 mol/kg of reaction medium.

The compound for increasing the selectivity of the catalyst may be introduced into the reactor via the peroxide compound feed, or via the organic solvent feed, or separately. When the process is continuous, it is preferably introduced continuously.

Certain compounds capable of increasing the selectivity of the catalyst induce a decomposition of $H_2O_2$, which harms the viability of the process. In order to reduce this decomposition, it may prove to be advantageous to introduce into the reaction medium a chelating agent as described in patent U.S. Pat. No. 5,591,875.

Another essential characteristic of the invention lies in the fact of having, in the liquid phase or in all of the liquid phases, a total organic solvent content of greater than or equal to 0.1 g/kg and less than or equal to 675 g/kg. This organic solvent content is generally greater than or equal to 1 g/kg, in particular greater than or equal to 10 g/kg and preferably greater than or equal to 50 g/kg. The organic solvent content is usually less than or equal to 650 g/kg, more especially less than or equal to 600 g/kg and usually less than or equal to 550 g/kg.

In the process according to the invention, it is preferable for the liquid phase or all of the liquid phases to have a total content of water plus peroxide compound (preferably hydrogen peroxide) that is greater than or equal to 100 g/kg, in particular greater than or equal to 125 g/kg, more particularly greater than or equal to 150 g/kg and preferably greater than or equal to 200 g/kg. The total content of water plus peroxide compound (preferably hydrogen peroxide) is usually less than or equal to 990 g/kg, more especially less than or equal to 950 g/kg, or even less than or equal to 925 g/kg, values of less than or equal to 900 g/kg being the most common.

The oxirane that may be prepared by the process according to the invention is an organic compound comprising a group corresponding to the general formula:

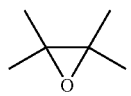

The oxirane generally contains from 2 to 20 carbon atoms and preferably from 3 to 10 carbon atoms. An oxirane that may be advantageously prepared by the process according to the invention is 1,2-epoxypropane or 1,2-epoxy-3-chloropropane.

The olefins that are very suitable in the process according to the invention generally contain from 2 to 20 carbon atoms and preferably from 3 to 10 carbon atoms. Olefins containing from 2 to 4 carbon atoms are preferred, and in particular propylene or allyl chloride, in which case the oxirane produced is 1,2-epoxypropane or 1,2-epoxy-3-chloropropane.

It may be advantageous to introduce the olefin into the reactor, in which the epoxidation reaction takes place, in diluted form in one or more alkanes. For example, a fluid containing the olefin and also at least 10% (in particular 20%, for example at least 30%) by volume of one or more alkanes may be introduced into the epoxidation reactor. For example, in the case of propylene, said propylene may be mixed with at least 10% by volume of propane when the recycled unconverted propylene is introduced into the reactor. It may also be a source of propylene that is not completely purified of propane.

The peroxide compounds that may be used in the process according to the invention are organic and inorganic peroxide compounds containing one or more peroxide (—OOH) functions that can release active oxygen and that are capable of carrying out an epoxidation. Hydrogen peroxide and peroxide compounds that can produce hydrogen peroxide under the epoxidation reaction conditions are very suitable. Hydrogen peroxide is preferred.

When hydrogen peroxide is used, it may be advantageous to use in the process according to the invention an aqueous hydrogen peroxide solution in crude form, that is to say unpurified form. For example, a solution obtained by simple extraction, with substantially pure water, of the mixture derived from the oxidation of at least one alkylanthrahydroquinone may be used (process known as "autoxidation AO process") without a subsequent washing and/or purification treatment. These crude hydrogen peroxide solutions generally contain from 0.001 to 10 g/l of organic impurities expressed as TOC (Total Organic Carbon). They usually contain metal cations (such as alkali metals or alkaline-earth metals, for instance sodium) and anions (such as phosphates or nitrates) in contents of from 0.01 to 10 g/l.

The organic solvents that may be used in the process according to the invention may be aromatic or aliphatic organic derivatives, these organic derivatives containing, for example, from 1 to 4 carbon atoms. They are preferably alcohols such as methanol or isopropanol. Methanol is preferred. Acetonitrile may also be used.

The catalysts used in the process according to the invention generally contain a zeolite, that is to say a solid containing silica that has a microporous crystalline structure. The zeolite is advantageously free of aluminum. It preferably contains titanium.

The zeolite that may be used in the process according to the invention may have a crystalline structure of ZSM-5, ZSM-11 or MCM41 type or of beta zeolite type. Zeolites of ZSM-5 type are very suitable. Those with an infrared adsorption band at about 950-960 cm$^{-1}$ are preferred.

The zeolites that are particularly suitable are titanium silicates. Those corresponding to the formula xTiO$_2$(1–x)SiO$_2$ in which x is from 0.0001 to 0.5 and preferably from 0.001 to 0.05 are highly efficient. Materials of this type, known as TS-1 and having a crystalline structure of ZSM-5 type, give particularly favorable results.

Advantageously, the catalyst has the form of spherical particles obtained by any known method.

The catalyst particles generally have a mean diameter of greater than or equal to 0.01 mm and less than or equal to 5 mm, a specific surface area of greater than or equal to 1 m$^2$/g and less than or equal to 900 m$^2$/g (determined according to the nitrogen adsorption method), an apparent density of between 0.1 and 1.0 g/ml, a pore volume of between 0.25 and 2.5 ml/g and a pore diameter distribution with a maximum of between 15 and 2000 Å.

According to one preferred variant of the present invention, the oxirane is 1,2-epoxypropane (or 1,2-epoxy-3-chloropropane), the olefin is propylene (or allyl chloride), the peroxide compound is hydrogen peroxide and the catalyst is titanium silicalite, preferably of TS-1 type with a crystalline structure of ZSM-5 type.

The temperature at which the olefin reacts with the peroxide compound is generally greater than or equal to 0° C. and preferably greater than or equal to 35° C. It is advantageous to perform the reaction at a temperature of greater than or equal to 40° C. and preferably greater than or equal to 45° C. A temperature of greater than or equal to 50° C. is most particularly preferred. However, the reaction temperature is generally less than or equal to 120° C., often less than or equal to 100° C. and preferably less than or equal to 80° C.

In the process according to the invention, when it is performed continuously, the peroxide compound is generally used in an amount of at least 0.005 mol per hour and per gram of zeolite, in particular of at least 0.01 mol per hour and per gram of zeolite. The amount of peroxide compound is usually less than or equal to 5 mol per hour and per gram of zeolite and in particular less than or equal to 3 mol per hour and per gram of zeolite. Preference is shown for an amount of peroxide compound of greater than or equal to 0.03 mol per hour and per gram of zeolite and less than or equal to 2 mol per hour and per gram of zeolite.

In the process according to the invention, the peroxide compound is advantageously used in the form of an aqueous solution. In general, the aqueous solution contains at least 10% by weight of peroxide compound and in particular at least 20% by weight. It usually contains a maximum of 70% by weight of peroxide compound and in particular 50% by weight.

Generally, the molar ratio between the amount of olefin used and the amount of peroxide compound used is greater than or equal to 0.1 and less than or equal to 100. Advantageously, this ratio is greater than or equal to 0.5 and less than or equal to 50. Preferably, this ratio is greater than or equal to 1 and less than or equal to 25.

In the process according to the invention, it may moreover prove advantageous to maintain the pH of the liquid phase during the reaction between the olefin and the peroxide compound at a value of at least 4.8 and in particular of at least 5. The pH is advantageously less than or equal to 6.5 and in particular 6. Good results are obtained when the pH is from 4.8 to 6.5 and preferably from 5 to 6. The pH of the liquid phase during the epoxidation reaction may be controlled by adding a base or a mixture of a salt and its conjugate acid or base. The base may be chosen from water-soluble bases. They may be strong bases. They may also be weak bases.

In one particular embodiment of the process according to the invention, the pressure during the reaction is adapted to the solubility of the olefin in the liquid phase constituting the reaction medium. Generally, this pressure is greater than or equal to atmospheric pressure (1 bar), preferably greater than or equal to 2 bar, or even greater than or equal to 5 bar. This pressure generally does not exceed 40 bar, or even 30 bar, for practical reasons. A pressure of less than 20 bar gives good results.

In the process according to the present invention, the olefin may be fed into the reactor in gaseous form, and its dissolution in the liquid phase then proceeds in situ in the reactor. Alternatively, and preferably, the olefin is predissolved in at least one fraction of the liquid phase before it is fed into the reactor. In a particularly preferred manner, the reactor is fed with a single flow of liquid in which the olefin has been predissolved under a pressure adapted to the desired content in the reaction medium.

The reaction between the olefin and the peroxide compound may be performed in continuous or batchwise mode. It is preferably performed continuously. In this case, the reactor is advantageously fed with a single flow of liquid in which the olefin has been predissolved. The pressure used to dissolve the olefin is preferably in the region of that present in the reactor. An olefin content greater than or equal to 10 g/kg, preferably greater than or equal to 40 g/kg, or even greater than or equal to 75 g/kg, is thus generally obtained in the reactor feed flow. However, this content is generally less than or equal to 500 g/kg, preferably less than or equal to 400 g/kg, or even less than or equal to 300 g/kg.

Advantageously, in the process according to the present invention, the oxirane produced is removed from the reaction medium by depressurization (in the case where the oxirane produced is gaseous at atmospheric pressure) and/or by stripping using a gaseous compound. Specifically, it has been found that the oxirane reacts in the epoxidation reaction medium with the water that accompanies the peroxide compound and/or the organic solvent to form by-products, thereby reducing the selectivity of the epoxidation reaction. By introducing a gaseous compound into the reaction medium at a flow rate that is sufficient to strip out the oxirane produced and to remove it from the reaction medium at the same time as the gaseous compound, and/or by sufficiently reducing the pressure of the reaction medium, the contact time between the oxirane produced and the epoxidation reaction medium is reduced. The formation of by-products is thus avoided and the epoxidation selectivity is increased. Preferably, the oxirane formed is removed by depressurization/stripping in a proportion of at least 50%, or even 75%. However, at least 1% generally remains in the liquid phase, or even at least 5%. The gaseous compound that may be used in this particular embodiment of the process according to the invention may be any compound that is in gaseous form under the epoxidation conditions and that has no negative impact on the epoxidation reaction. It may be chosen from inert gases such as nitrogen. It may also be the olefin when said olefin is gaseous and used in excess.

In the case of such a continuous process, at least some of the liquid phase leaving the reactor is advantageously recirculated. To this end, a loop reactor is preferably used, that is to say a reactor equipped with a device that is adequate for carrying out this recirculating.

Preferably, the reactor comprises a bed of the catalyst according to the invention. This bed may be a fixed bed or a fluid bed. It is advantageously a fluid bed.

In one preferred embodiment of the present invention, water is introduced solely as diluent for the peroxide compound, that is to say that the reactor is not fed with water per se, but only via the peroxide compound that is in aqueous solution. This variant is particularly advantageous in the case of a continuous process in which at least some of the liquid phase is recycled.

In general, in order to maximize the production efficiency of the process, the amount of olefin is pushed to the maximum (for example by making it greater than 100 g/kg). Similarly, it is advantageous for the concentration of the peroxide compound solution used to be high (for example up to 70% by weight). Since the process is generally performed at a high degree of conversion and since a lot of water is consequently produced in the reactor after the peroxide compound has been consumed, an additional supply of water to the reactor may be avoided if the process is performed continuously with recycling of at least some of the liquid phase.

An example of a process according to the present invention is represented diagrammatically in FIG. 1. A liquid flow called the "shuttle" is introduced into the bottom of a reactor (1) containing a zeolite-based catalyst via a pipe (2). This flow comprises an olefin, a peroxide compound, water, formed oxirane, one or more organic solvents and one or more compounds capable of increasing the selectivity of the catalyst toward the epoxidation reactions. The liquid flow circulates in the reactor in the direction of the arrows. On leaving the reactor, the reaction medium is depressurized by means of a valve (3). This depressurization is followed by the sparging of a gaseous compound using a flow meter (4) in a stripping column (5). A gas mainly consisting of the produced oxirane, unconverted olefin, the gaseous compound used for the stripping and traces of organic solvent, leaves the stripping column (5) via the pipe (6). The liquid phase leaving the top of the column is partly recycled into the reactor via the pipe (7) and partly removed via the overflow pipe (8). The peroxide compound is added to the recycled fraction via the pipe (9), and organic solvent is added via the pipe (10). The compound capable of increasing the selectivity of the catalyst may be added via the peroxide compound or via the organic solvent. The mixture thus obtained then passes into a saturator (12) via a pump (11). This saturator is fed with olefin under pressure via a flow meter (13), and at its outlet are collected, on the one hand, a gaseous phase of undissolved olefin that leaves through the pipe (14) via a depressurization valve (15), and on the other hand, the shuttle that is fed into the reactor (1) via the pipe (2).

EXAMPLES

Two series of 4 tests were carried out, one (not in accordance with the invention) in a medium with a high content of organic solvent ($CH_3OH$, 860 g/kg), the other (in accordance with the invention) in a medium with a low content of organic solvent ($CH_3OH$, 530 g/kg). These 4 tests were carried out according to the following scheme:

a first reference test, without addition of a compound capable of increasing the selectivity of aii epoxidation catalyst, a second test with addition of NaCl so as to bring the Na concentration in the reaction medium to a level of 55 ppm, a third test with addition of sodium acetate ($CH_3COONa$) so as to bring the Na concentration in the reaction medium to a level of 55 ppm, a fourth test with addition of ethanolamine ($NH_2CH_2CH_2OH$) so as to bring its concentration in the reaction medium to 100 ppm.

For these tests, a plant according to FIG. 1 was used and propylene was chosen as olefin, $H_2O_2$ was chosen as peroxide compound and TS-1, in the form of beads consisting of 35% titanium silicalite dispersed in a silica matrix (65% by weight) and obtained by a process of sol-gel type, was chosen as catalyst. The oxirane produced is 1,2-epoxypropane or propylene oxide (PO). The stripping gas was nitrogen.

Since Pe (propylene) is less soluble in a medium with a low methanol content, the pressure in the saturator was adjusted to keep the Pe concentration constant in the two series of measurements. The molar flow rate of $H_2O_2$ was also kept constant at 0.17 mol/h. The methanol flow rate and the flow rate of nitrogen used for the stripping were adjusted to maintain a constant residence time in the plant. The flow rate of the overflow liquid was about 106 g/h. The shuttle circulation speed was 5 l/h.

The conditions of these tests are given in Table 1 below.

TABLE 1

|  | Series 1 | Series 2 |
|---|---|---|
| TS-1 used (g) | 1.58 | 1.58 |
| T° reactor (° C.) | 55 | 55 |
| Conc. $H_2O_2$ solution used (% by weight) | 39 | 10 |
| Flow rate of $H_2O_2$ solution (g/h) | 15.2 | 59 |
| $H_2O_2$ used (mol/h) | 0.17 | 0.17 |
| Pe (mol/kg) | 0.24 | 0.24 |
| $CH_3OH$ used (ml/h) | 230 | 120 |
| Saturator pressure (bar) | 2.6 | 8 |
| $N_2$ flow rate (1N/h) | 50 | 45 |
| Plant residence time (h) | 4 | 4 |
| Residence time on catalyst (min) | 5.5 | 5.5 |

The liquid phase fed into the reactor (after 6 h) was analyzed and the composition below given in Table 2 was found.

TABLE 2

|  | Series 1 | Series 2 |
|---|---|---|
| $H_2O + H_2O_2$ (g/kg) | 90 | 460 |
| $CH_3OH$ (g/kg) | 860 | 530 |
| Pe (g/kg) | 10 | 10 |
| PO (g/kg) | 5.5 | 6.5 |

After a running time of 24 h, the results below given in Table 3 were obtained.

TABLE 3

|  | Degree of conversion of the $H_2O_2$ (%) (1) | | PO/C3f selectivity (%) (2) | |
|---|---|---|---|---|
|  | Series 1 | Series 2 | Series 1 | Series 2 |
| Without addition | 76.3 | 85.2 | 83.4 | 79.0 |
| +NaCl | 51.0 | 87.3 | 97.2 | 95.8 |
| +$CH_3COONa$ | 31.1 | 86.2 | 97.9 | 97.4 |
| +$NH_2CH_2CH_2OH$ | 46.3 | 88.7 | 98.4 | 98.5 |

(1) Calculation of the degree of conversion
The degree of conversion of the $H_2O_2$ is calculated from the $H_2O_2$ inlet and outlet flow rates.
TC(%) = 100 × ($H_2O_2$ used in mol/h - unconverted $H_2O_2$ in mol/h)/$H_2O_2$ used in mol/h with uncoverted $H_2O_2$ = $H_2O_2$ conc. of the overflow liquid in mol/kg × overflow liquid flow rate in kg/h
(2) Calculation of the PO/$C_3f$ selectivity
PO/$C_3f$ sel. (%) = 100 × $PO_{formed}$/Σ(PO + by-products)$_{formed}$

The invention claimed is:

1. A continuous or batchwise process for manufacturing an oxirane by reaction between an olefin and a peroxide compound in a reactor containing a liquid phase, in the presence of water, one or more organic solvents, a catalyst and one or more compounds for increasing the selectivity of the catalyst toward epoxidation reactions, wherein
when the process is performed in batchwise mode, the liquid phase present in the reactor when the reaction starts has a total organic solvent content of at least 0.1 g/kg and of not more than 675 g/kg, and
when the process is performed continuously, all of the liquid phases that are fed continuously into the reactor have a total organic solvent content of at least 0.1 g/kg and of not more than 675 g/kg.

2. The process according to claim 1, wherein the total organic solvent content in the liquid phase present in the reactor and all of the liquid phases that are fed continuously into the reactor is not more than 600 g/kg.

3. The process according to claim 1, wherein the peroxide compound is hydrogen peroxide and the total content of water plus hydrogen peroxide in the liquid phase present in the reactor and all of the liquid phases that are fed continuously into the reactor is at least 100 g/kg.

4. The process according to claim 3, wherein the total content of water plus hydrogen peroxide in the liquid phase present in the reactor and all of the liquid phases that are fed continuously into the reactor is at least 150 g/kg.

5. The process according to claim 1, wherein the compound for increasing the selectivity of the catalyst is chosen from mineral or organic bases, mixtures of a salt and of its conjugate acid or base, salts, and mixtures thereof.

6. The process according to claim 1, wherein the organic solvent is methanol.

7. The process according to claim 1, wherein the oxirane is 1,2-epoxy-propane or 1,2-epoxy-3-chloropropane, the olefin is propylene or allyl chloride, the peroxide compound is hydrogen peroxide and the catalyst is titanium silicalite of TS-1 type with a crystalline structure of ZSM-5 type.

8. The process according to claim 1, wherein the olefin reacts with the peroxide compound at a temperature of from 10 to 1200C and at a pressure of from 1 to 40 bar.

9. The process according to claim 1, wherein the process is continuous, all of the liquid phases are fed into the reactor as a single flow in which the olefin has been dissolved, at least some of the liquid phase leaving the reactor is recirculated, and water is introduced solely as diluent for the peroxide compound.

10. The process according to claim 9, wherein the total olefin content in the liquid flow fed into the reactor is at least 10 g/kg, and the oxirane is removed from the reaction medium by depressurization and/or stripping using a gaseous compound.

11. The process according to claim 1, wherein the process is performed in batchwise mode.

12. The process according to claim 1, wherein the process is performed continuously.

13. The process according to claim 1, v:herein the oxirane is 1,2-epoxy-propane.

14. The process according to claim 1, wherein the oxirane is 1,2-epoxy-3-chloropropane.

15. The process according to claim 2, wherein the process is performed in batchwise mode.

16. The process according to claim 2, wherein the process is performed continuously.

17. The process according to claim 7, wherein the process is performed in batchwise mode.

18. The process according to claim 7, wherein the process is performed continuously.

* * * * *